United States Patent [19]

Ecanow

[11] Patent Number: 4,794,000
[45] Date of Patent: Dec. 27, 1988

[54] COACERVATE-BASED ORAL DELIVERY SYSTEM FOR MEDICALLY USEFUL COMPOSITIONS

[75] Inventor: Bernard Ecanow, Wilmette, Ill.

[73] Assignee: Synthetic Blood Corporation, Deerfield, Ill.

[21] Appl. No.: 1,814

[22] Filed: Jan. 8, 1987

[51] Int. Cl.$^4$ .............................................. A61K 37/00
[52] U.S. Cl. .................................... 424/457; 424/451; 424/456; 424/459; 424/460; 424/461; 424/462; 424/463; 514/54; 514/59; 514/715; 514/774; 514/776; 514/937; 514/959; 514/963; 514/964
[58] Field of Search ............... 424/457, 456, 451, 459, 424/460, 461, 462, 463; 514/54, 59, 715, 774, 776, 937, 959, 963, 964

[56] References Cited

U.S. PATENT DOCUMENTS

| | | | |
|---|---|---|---|
| 4,343,797 | 8/1982 | Ecanow | 514/2 |
| 4,356,167 | 10/1982 | Kelly | 514/3 |
| 4,394,372 | 7/1983 | Taylor | 514/3 |
| 4,439,424 | 3/1984 | Ecanow et al. | 514/2 |
| 4,448,765 | 5/1984 | Ash et al. | 514/3 |
| 4,539,204 | 9/1985 | Ecanow et al. | 514/6 |
| 4,547,490 | 10/1985 | Ecanow et al. | 514/21 |
| 4,558,032 | 12/1985 | Ecanow et al. | 514/2 |

FOREIGN PATENT DOCUMENTS 0130160 1/1985 European Pat. Off. .

OTHER PUBLICATIONS

Jizomoto, Hiroaki, "Phase Separation Induced in Gelatin-Base Coacenation Systems by Addition of Water-Soluble Nonionic Polymers I: Microencapsulation" CA101(22):198075y.
Iwasaki, Horoshi et al., "Microencapsulation" CA90(8):61260q.

Primary Examiner—John Kight
Assistant Examiner—S. A. Acquah
Attorney, Agent, or Firm—Mason, Kolehmainen, Rathburn & Wyss

[57] ABSTRACT

The present invention provides for an oral drug delivery system based on a two phase liquid coacervate system prepared from water and one or more surfactants selected from anionic, cationic, amphoteric, and nontoxic surfactants, polysaccharides, synthetic polymers and polysorbates and their derivatives, and in which a pharmaceutical component is incorporated. The delivery system may be prepared in the form of a microemulsion as well as other forms including encapuslated microparticles. The claimed oral composition is useful to delivery oral dosage forms of drugs, their salts and derivatives thereof; biologicals, enzymes, and other pharmocologically active compositions. A method to prepare the oral drug delivery system is also disclosed.

29 Claims, No Drawings

COACERVATE-BASED ORAL DELIVERY SYSTEM FOR MEDICALLY USEFUL COMPOSITIONS

BACKGROUND OF THE INVENTION

It is widely acknowledged that the vehicle by which drug compounds are introduced into the body are of critical significance. Such vehicles have an important influence on such variables as drug stability and efficacy, frequency of adverse drug reactions and bioavailability.

This invention concerns an oral delivery system for pharmaceutical components which comprises a microemulsion and other related dosage forms, based upon an aqueous, liquid two phase coacervate system. The dosage forms of the invention are useful to prepare and deliver drugs, biologicals, enzymes, and other pharmacologically active compositions. The physical-chemical, pharmaceutic and thermodynamic characteristics of the disclosed delivery system account for its unusual solvent and other desirable properties. The use of a coacervate system to prepare the microemulsion and related dosage forms of this invention contributes to the compositions' unusual bioavailability characteristics.

DESCRIPTION OF THE PRIOR ART

The oral dosage forms disclosed in this invention are based upon a coacervate system. The specific inventive system herein does not appear in the prior art which utilizes a coacervate system in composition. Said art, instead, is directed primarily to synthetic whole blood substitutes limited in ability to act as delivery systems for pharmaceuticals.

U.S. Pat. No. 4,343,797 discloses a method for preparing a parenteral composition comprising a synthetic blood substitute in the form of a two-phase heterogeneous coacervate system. Said system, which has oxygen transport and other properties of whole blood, is produced by dispersing lecithin in water containing controlled amounts of sodium chloride, urea and albumin. This solution is then stored at low temperature, thereby producing a two-phase coacervate system that can be rendered isotonic with whole human blood by addition of controlled amounts of sodium chloride.

U.S. Pat. No. 4,439,424 discloses a preferred parenteral synthetic whole blood product in the form of a coacervate system that contains both a coacervate phase and an equilibrium bulk water phase based upon albumin, water, sodium chloride, urea and lecithin.

U.S. Pat. No. 4,547,490 describes an improvement wherein the coacervate system is produced from lecithin dispersed in an aqueous solution containing sodium chloride and albumin to which is added a non-polar or semi-polar solvent such as n-butyl alcohol.

U.S. Pat. Nos. 4,558,032, 4,539,204 and 4,596,778 relate to gelatin-based synthetic blood substitues based upon a two-phase coacervate system utilizing, respectively, gelatin and acacia, two gelatins or modified fluid gelatins of different isoelectric points, and gelatin or modified gelatin and lecithin.

U.S. Ser. Nos. 710,048 filed March 11, 1986 and 811,675 filed December 20, 1985, both by Ecanow et al, describe a synthetic whole blood product wherein the coacervate system is produced, preferably, from lecithin dispersed in an aqueous solution containing albumin and sodium chloride, the former incorporating a hemoglobin component and the latter incorporating polymerized hemoglobin or pyridoxylated-polymerized hemoglobin.

These known blood substitutes are essentially designed to serve as a resuscitative fluid, that is, a system by which oxygen is transported, like whole natural blood. The ability of said compositions to transport oxygen is premised upon the structural aspects of the coacervate system which protects components incorporated therein, such as stroma-free hemoglobin, from dissolving in the circulatory system after transfusion. Said functional advantage also sharply reduces or eliminates endotoxic phenomena as opposed to other known resuscitative fluids.

In contrast to the blood substitutes, the present invention has been formulated to faciliate solubilization of the pharmaceutical components incorporated therein. The two phase coacervate-based microemulsion is aqueous, thus significantly increasing the bioavailability of the pharmaceutical for smooth liberation into the circulatory system of the recipient.

Other examples of drug delivery systems also utilizing a coacervate system as a basis are disclosed in International Application No. PCT/US85/00859 published Nov. 21, 1985 and its counterpart application, U.S. Ser. Nos. 835,550 filed Mar. 3, 1986, 711,066 filed Mar. 12, 1985 by Ecanow and 896,844 filed Aug. 14, 1986 by Ecanow, the former two applications relating to oral dosage forms for insulin and atrial peptides, respectively.

The formulations of said systems, however, are premised primarily upon components which are found endogenous to the human system, whether natural or synthetic. For example, an exogenous source of gelatin can be used in said compositions, but is derived from skin, ligaments, etc. The present pharmaceutical delivery system, on the other hand, is prepared from a select group of surfactants, that is, anionic, cationic, amphoteric, and non-ionic, as well as, preferably, polysaccharides, synthetic polymers and polysorbates and, thus, differ significantly chemically from those described in the prior art.

U.S. Ser. No. 896,844 relates not to an oral dosage form for drugs, but to a parenteral form that, preferably, uses an alcohol component in preparation of the formulation. The problems addressed in said application do not include protection of the drug incorporated therein from degradation by enzymes, pH, factors such as the acid-base balance and other gastrointestinal conditions and processes.

Examples of liposome systems which are used as drug delivery systems include the following U.S. patents. U.S. Pat. No. 4,356,167 discloses a liposome delivery system for medicaments, wherein the liposome is comprised of an aliphatic liquid-sterol-water lamellas. U.S. Pat. No. 4,394,372 discloses a process for producing liposomes which are comprised of a bilayer membrane, one layer which is aqueous and the other layer which is organic. U.S. Pat. No. 4,448,765 discloses a liposome delivery system which incorporates a polymer in the vesicle wall to stabilize the composition. Physiological components are introduced into the liposomes for therapeutic administration to human or other mammalian hosts. Again, liposomes are directed to a parenteral form of administration and, therefore, do not address problems encountered in oral administration of pharmaceuticals, as well as being fundamentally different in terms of structure, composition and method of manufacture.

Further, microemulsions of the prior art are known to be comprised of a lipid or oil phase and a water phase. In contrast, the disclosed microemulsion is comprised of two aqueous phases and as such constitutes a significant improvement in the art. Since both phases of the said composition are aqueous, the possibility that the microemulsion may be toxic is reduced or eliminated. In addition, because both phases are aqueous, the bioavailability of the incorporated drug is significantly increased. In the method of presently known drug delivery microemulsions, the drug is dissolved in the oil phase and is retained therein for varying periods of time. In the claimed invention, however, the pharmaceutical component is incorporated in an aqueous phase that permits ready release of the drug. The method of this invention provides for a process that modifies the ready release characteristic so that the composition of this invention can be prepared in a spectrum of drug release rates and a related spectrum of drug metabolism rates.

SUMMARY OF THE INVENTION

The present invention constitutes an improved formulation for the oral delivery of pharmacologically active compositions including, in addition to drugs, their salts and derivatives, biologicals, enzymes and other pharmalogically active compositions. The formulations may be prepared as microemulsions and microencapsulated compositions, and demonstrate reduced toxicity, improved bioavailability and stability.

DETAILED DESCRIPTION OF THE INVENTION

The present invention provides for a composition useful as an oral drug delivery system, said preparation comprising a non-toxic liquid aqueous two phase coacervate system;

(a) one of said phases being an aqueous colloid rich phase, semipolar to non-polar in character;

(b) the other of said phases being an aqueous colloid poor phase, semipolar to polar in character;

(c) said colloid rich phase being insoluble and in equilibrium with said colloid poor phase;

(d) said two phase system being prepared from water and one or more surfactants selected from the group comprising anionic, cationic, amphoteric, and non-ionic surfactants, polysaccharides, synthetic polymers and polysorbates and their derivatives;

(e) and wherein a pharmaceutical component is incorporated into the colloid rich phase of said two phase system.

It must be emphasized that in the said coacervate both phases are aqueous. One of the phases of the said coacervate system is referred to as the colloid rich phase. This phase is semi-polar to non-polar in character and is capable of solubilizing oil soluble and various other water insoluble compositions of matter. Accordingly, in this invention, this phase is used to solubilize and incorporate non-polar pharmacologically active compositions. The other phase, known as the colloid poor phase, is polar to semi-polar and will solubilize water soluble compositions. To a limited degree, this phase will also solubilize various water insoluble compounds. While disclosure of oral pharmaceutical delivery systems in the form of microemulsions and microencapsulated preparations are preferred embodiments of the invention, other acceptable oral delivery systems become available in the course of manufacturing.

The invention also provides for a preferred method of preparing the oral delivery system comprising the steps of (a) mixing a solution of dextran into a solution of polyethylene glycol;

(b) storing the mixture undisturbed and at room temperature or under conventional refrigeration for from 6 to 24 hours until the composition of step (a) separates into two layers, one above each other, the lower phase being the colloid rich phase, the upper phase being the colloid poor phase; separating the two phases; and mixing the desired quantity of the pharmaceutical component into the colloid rich phase.

In this disclosure, the term "microemulsion" refers to a two phase system in which one liquid is dispersed in the form of small globules or particles throughout another liquid. The term "drug" is used to mean any compound defined as a "drug" by the Federal Food, Drug and Cosmetic Act and its amendments; the term "biological" is defined to mean a medically useful composition derived from a biological source or the synthetic equivalent thereof; the term "enzyme" is defined to mean any protein or conjugated protein produced biologically or synthetically that functions as a chemical catalyst in mammals. "Enzyme systems" is used to mean a functionally related combination or sequence of such proteins.

As used herein the terms "liquid, aqueous coacervate system", "coacervate" and "coacervate system" refer to the same entity and are used interchangeably. The terms "coacervate phase" and "colloid rich phase" refer to the same entity and are used interchangeably in this disclosure. The terms "colloid poor phase" and "equilibrium water phase" are used interchangeably in this disclosure. The terms "surface active composition" and "surfactant" are also used interchangeably in this disclosure. Also, the term "pharmaceutical component" is used to refer to any drug salt or derivative thereof, biological, enzyme, enzyme system and any pharmacologically active composition or derivative thereof. The term "deliver" is used as per the conventional pharmaceutical meaning.

It is known that through a process referred to as coacervation compositions comprised of two or more phases and known as coacervates may be produced. As noted, the claimed invention and the other oral delivery systems available through the manufacturing process of this invention make use of a coacervate system. The term "coacervation" may be defined as a process of separation of colloidal solutions into two or more immiscible liquid layers. (Ref. Dowben, R. *General Physiology*, Harper & Row, New York, 1969, pp. 142-143.)

The ingredients that comprise the two phase coacervate system are present in both phases; however, the colloid rich phase has a greater concentration of said components than the colloid poor phase. Analytic techniques indicated that the colloid rich phase has between twenty and sixty percent greater (or more) concentration of said ingredients than the colloid poor phase.

In addition, the water of the colloid rich phase of the coacervate of this invention is "structured" in a different form than the bulk water of the colloid poor phase, the two phases being in equilibrium with and immiscible in each other.

Components that may be used to formulate the coacervate system of the drug delivery system comprise anionic, cationic, amphoteric, and non-ionic surfactants. Anionic surfactants include di-(2 ethylhexyl) sodium sulfosuccinate; non-ionic surfactants include the fatty acids and the esters thereof; surfactants in the amphoteric group include (1) substances classified as simple, conjugated and derived proteins such as the albumins, gelatins, and glycoproteins, and (2) substances contained within the phospholipid classification, for example lecithin. The amine salts and the quaternary ammonium salts within the cationic group also comprise useful surfactants. Other surfactant compounds useful to form coacervates useful in the preparation of this invention include compositions within the groups known as the polysaccharides and their derivatives, the mucopolysaccharides and the polysorbates and their derivatives. Synthetic polymers that may be used as surfactants include compositions such as polyethylene glycol and polypropylene glycol.

Further examples of suitable compounds that may be utilized to prepare coacervate systems for this invention include glycoproteins, glycolipids, galactose, gelatins, modified fluid gelatins and galacturonic acid.

In addition, substances that are not intrinsically surface active may be used to prepare coacervates for the present oral delivery system provided they can be made so by chemical or other means. Thus, fatty acids are not considered to be surface active compounds; however, when they are reacted with an alkaline chemical entity the resulting products will include one that has surface-active properties. For example, mixing stearic acid with sodium hydroxide will produce a salt of stearic acid that has surfactant characteristics.

In this invention, the aqueous based coacervate phase is used to solubilize and incorporate the pharmaceutical component. If desired, the resulting oral composition may be dispensed as such. Depending upon the intended use of the final product, additional processing steps are carried out to produce preferred finished products. The procedures that are used include (1) mixing the pharmaceutical component(s) into the aqueous based colloid rich phase of the described coacervate system, the resulting product, to which a flavoring agent may be added, dispensed as such; (2) mixing the colloid rich phase containing the pharmaecutical component with the colloid poor phase and processing further using a colloid mill to produce an oral drug delivery preparation in the form of an emulsion and, if desired, adding a flavoring agent and dispensing the emulsion as such; and (3) adding a phospholipid and the colloid poor phase of the coacervate system to the colloid rich phase containing the pharmaceutical component. A microemulsion of the resulting product is then made using a colloid mill or other suitable technology. This microemulsion should be comprised of globules ranging in size from two microns to one hundred nanometers. A suitable flavoring agent may be added if desired and the composition dispensed as such. A fourth procedure comprises adding a protein and the colloid poor phase of the coacervate system to the colloi rich phase containing the pharmacological component. The preparation is then emulsified using a colloid mill to produce encapsulated particles ranging in size from between one and two microns to one hundred nanometers. The microparticles are then subjected to a heating or chemical process that hardens the interfacial surfaces of the particles. The process provides for any degree of surface hardness, thereby imparting a range of sustained release rates to the product. The final product of this process can consist of microparticles of the same or different drug release rates and can be dispensed in an appropriate liquid, capsule, or other suitable dosage forms. It is understood that dispensing of any of the preparations described above is always performed in terms of the appropriate dose of the incorporated pharmocological component.

The following is a preferred method to prepare the disclosed oral drug delivery system. The coacervate system is prepared by mixing 25 gms of dextran into 100 mls of distilled water. Next 7.5 gms of polyethylene glycol, preferably polyethylene glycol 8000, is added to the preparation. The proportions of dextran and polyethylene glycol may vary; that is, the proportion of dextran may be greater than that of polyethylene glycol. In the practice of this invention equal proportions of these components are preferred. The resulting preparation is stored undisturbed until visual inspection indicates that the coacervation process is taking place, by the existence of distinct colloid rich and colloid poor phases. It is preferred that the storage step be continued until visual inspection indicates that no further phase separation is taking place.

If after six to twelve hours there is little or no evidence that coacervation is occurring, NaCl solution is added dropwise to the preparation until said preparation indicates that a separation of phases is occurring. It is preferred that the preparation be stored undisturbed until visual inspection indicates that no further separation of the two phases is taking place. At this point, the composition will comprise a colloid rich phase and a colloid poor phase, both of which are aqueous.

The two phases are then separated into individual glass containers by means of a separatory funnel. The desired quantity of one or more of the desired pharmaceutical component(s) is then mixed into the colloid rich phase. Typically, this quantity will in an amount that provides the medically recognized dose in each dispensable unit of this invention; that is, teaspoon, capsule, etc. The present method provides for either increase or reduction of the medically recognized does of the pharmacological component where such is desirable.

On completion of this step, the resulting product comprises an oral liquid drug product and is ready to be dispensed or stored. Addition of the previously separated colloid poor phase to the composition described immediately above followed by an emulsifying step using a colloid mill or other suitable technology will also product an emulsion acceptable as an oral drug preparation.

It is preferred that the composition be processed further according to the following directions. An appropriate quantity of a dispersing agent is added to 100 mls. of the colloid rich phase containing the pharmacological component(s). Examples of acceptable dispersing agents include proteins, phospholipids, glycerides, compositions known as tweens, non-toxic glycols, etc. In preparing the disclosed formulation, the addition of five gms of lecithin is preferred. The quantity of lecithin added by dispersion, however, can range from five to fifty gms. Following addition of lecithin to the colloid rich phase, the previously separated colloid poor phase is mixed into the preparation, which is then emulsified using a colloid mill or other acceptable technology to produce a microemulsion comprised of globules in the one micron or smaller, i.e., nanometer size range. The said microemulsion comprises an acceptable oral drug delivery system.

As stated, the present method also provides for a sustained release oral drug product. This product is produced according to the following instructions. The desired quantity of drug is contained in one hundred mls of the previously described colloid rich phase-lecithin composition. This is followed by the addition of a protein, preferably albumin, to the said composition. From 1% to 10% w/v of albumin may be added, however 1% is preferred. Following this step, the previously separated colloid poor phase of the coacervate system is mixed into the preparation, which is then emulsified using a colloid mill or other suitable technology to produce a microemulsion. The resulting microemulsion is then subjected to a heating step comprised of heating the composition to 30-40 degrees Celsius for from five to one hundred and twenty seconds to produce a preparation with sustained release properties. A sustained release form of the disclosed invention can also be made using chemical means; i.e., adding a non-toxic member of the aldehyde group such as gluteraldehyde in an amount ranging from 1 to 10% w/v to the microemulsion. The heating technique is preferred.

The product resulting from the heating step is comprised of microparticles with semi-rigid to rigid interfacial characteristics. These particles are filtered from the preparation and separated into any number of groups of equal or unequal quantity as desired. Each group is subjected to a heating step. The duration of the heating step is dependent upon the effect of heating on the stability of the incorporated pharmaceutical component(s) and the desired sustained release characteristics. The heating step may vary from 5 to 135 seconds. Each group of particles is heated to 30°-40° C. for such period as will (1) be consistent with maintaining the stability of the pharmacological component(s) and (2) give the desired spectrum of sustained release characteristics.

A chemical step may be used in place of the heating step through the use of a non-toxic aldehyde such as gluteraldehyde by adding from 1%-10% by weight to the preparation. If gluteraldehyde is used, the microparticles so treated are subjected to repeated washing with distilled water until no trace of gluteraldehyde can be detected. The heating step described above is preferred.

As a result of the heating or chemical step, the resulting product is comprised of microparticles with differing rates of drug release. In the practice of this invention, the microparticles can be dispensed in any acceptable oral dosage form in such manner as will give the desired range of sustained release and medical effects.

While it is preferred that finished products of this invention comprise a microemulsion, this preference does not exclude the preparation and use of macroemulsions as oral drug delivery systems in accordance with the invention.

This invention also provides for an optional process step whereby the pharmaceutical component is dissolved in a monoglyceride, a diglyceride, a triglyceride or any combination thereof. When the glyceride component is in liquid form, the quantities are in terms of volume to volume; when the glyceride exists initially in solid form, the quantities are in terms of weight to volume. This further step comprises mixing the glyceride component and the pharmacological entity into the colloid rich phase. Thereafter, dependent upon the final dosage formulation to be produced, the sequence of steps described above are followed. In the event a combination of glycerides are used, the proportion of each glyceride can vary provided that the total does not exceed 15%.

When it is desired to achieve higher drug concentrations in body tissues and fluids, the coacervate is prepared and the colloid rich phase is separated from the colloid poor phase as previously described. 5% by weight of lecithin is to be added to the colloid rich phase and the pharmaceutical component is dissolved in either a monoglyceride, diglyceride, triglyceride solution or a mixture thereof. When an individual glyceride is used an amount of 5% by volume, again, is preferred. The quantity of combined glycerides should not exceed 15%. The preparation containing the glyceride(s) and the pharmaceutical component(s) is then mixed into the colloid rich phase, after which 5 gms of lecithin and if desired, the previously separated colloid poor phase are added. The resulting preparation is then emulsified to produce a microemulsion which can be dispensed in the medically indicated dose in any appropriate oral dosage form.

If microparticles of the preparation containing the glyceride component are desired, the procedure for preparing such compositions described above is followed. To produce a sustained release formulation of the composition which includes a glyceride component, the procedure described above to produce sustained release compositions are followed. The said microemulsion can be dispensed in the required dose. After placing the micro particles in the desired oral dosage form, i.e., liquid tablet, capsule, etc. in the indicated dose, the composition can be dispensed.

Additionally, the colloid poor phase of the coacervate system of this invention may be used to produce, to solubilize, and to deliver semi-polar drugs and other medically useful compositions.

The present invention provides for the incorporation of more than one pharmaceutical component in a single dose; e.g. spironolactone and hydrochlorothiazide; sulfamethoxazole and trimethoprim; codeine phosphate and accetaminophen and other medically useful pharmaceutical combinations. Finished products of this invention can be made in tablet, granular, liquid, suspension, emulsion and other known oral dosage forms.

The following are examples of oral delivery systems for pharmaceutical compositions according to the present invention and methods by means of which the claimed compositions may be produced.

EXAMPLE 1

Prepare a 3% w/v solution of sterile water and dextran. Add a 3% w/v solution of polyethylene glycol to the dextran solution and mix thoroughly. Store the resulting composition undisturbed until visual inspection indicates that no further separation of phases is taking place. Separate the colloid rich phase from the colloid poor phase by means of a separatory funnel. Add to the colloid rich phase a quantity of erythromycin that will result in a finished product containing 250 mg of erythromycin per unit dose.

EXAMPLE 2

The procedure of Example 1 is followed except that erythromycin ethylsuccinate is used in place of erythromycin and the quantity of erythromycin succinate added is such as will result in a finished product containing 10 mg per unit dose.

EXAMPLE 3

The procedure of Example 1 is followed except that after erythromycin has been mixed into the colloid rich phase, the previously separated colloid poor phase is mixed into the preparation. The resulting product is then emulsified using a colloid mill to produce a microemulsion.

EXAMPLE 4

The procedure of Example 2 is followed except that after the erythromycin ethylsuccinate has been added, the previously separated colloid poor phase is mixed into the preparation. The resulting product is then emulsified using a colloid mill or other suitable technology.

EXAMPLE 5

The procedure of Example 1 is followed except that after erythromycin is added, 5 gms of lecithin is mixed into the composition. This step is followed by the addition of the previously separated colloid poor phase to the preparation and emulsifying the resulting product to produce a microemulsion.

EXAMPLE 6

The procedure of Example 5 is followed except 1% w/v of albumin is added before the microemulsion is prepared. The microemulsion is then heated for 50 seconds at 35°–36° C. to produce encapsulated microparticles.

EXAMPLE 7

The procedure of Example 6 is followed except that the microparticles of this composition, are then divided equally by weight into six portions; portion 1 is heated for 10 seconds at 70 degrees C.; portion 2 is heated at 70 degrees C. for 20 seconds; portion 3 is heated at 70 degrees C. for 40 seconds; portion 4 is heated for 50 seconds at 70 degrees C.; portion 5 is heated for 70 seconds at 70 degrees C.; and portion 6 is heated for 90 seconds at 70 degrees C. to produce a sustained drug release composition with differing rates of drug release.

EXAMPLE 8

The procedure of Example 7 is followed except that in place of the heating step, a 1% solution of gluteraldehyde is mixed into the microemulsion to produce a composition comprised of encapsulated microparticles.

EXAMPLE 9

The procedure of Example 5 is followed except that erythromycin stearate is used in place of erythromycin.

EXAMPLE 10

The procedure of Example 1 is follwed except that a 5% w/v solution of dextran is used in place of a 3% w/v dextran solution.

EXAMPLE 11

The procedure of Example 1 is followed except that a 5% w/v solution of polyethylene glycol is used in place of the 3% w/v solution of polyethylene glycol.

EXAMPLE 12

The procedure of Example 6 is followed except that the microemulsion is heated for 20 seconds.

EXAMPLE 13

The procedure of Example 7 is followed except that the product of Example 6 is separated into three portions; portion 1 is heated for 15 seconds at 70 degrees C.; portion 2 is heated for 25 seconds at 65 degrees C.; and portion 3 is heated for 35 seconds at 70 degrees C. to produce a composition with a range of sustained release rates.

EXAMPLE 14

The procedure of Example 1 is followed except that instead of dissolving 250 mg of erythromycin in the colloid rich phase, 250 mg of erythromycin is dissolved in a 5% solution of monoglyceride. This preparation is then mixed into the colloid rich phase of the coacervate to which 5 gms of lecithin and the colloid poor phase are added. The composition is then emulsified to produce a microemulsion.

EXAMPLE 15

The procedure of Example 14 is followed except that prior to the emulsifying step, 1% w/v of albumin is added to the preparation; the composition is then emulsified; after which the composition is heated to 36° C. for 45 seconds to produce a composition comprised of encapsulated microparticles.

EXAMPLE 16

The procedure of Example 5 is followed except that 5 gms of isolecithin is used in place of lecithin.

EXAMPLE 17

The procedure of Example 6 is used except that 1% w/v of glycoprotein is used in place of albumin.

EXAMPLE 18

The procedure of Example 5 is followed except that spironolactone and hydrochlorothiazide are used in place of erythromycin.

EXAMPLE 19

The procedure of Example 5 is followed except that sulfamethoxazole and trimethoprim are used in place of erythromycin.

EXAMPLE 20

The procedure of Example 14 is followed except that a preparation comprised of 4% monoglyceride, 3% diglyceride and 3% triglyceride is used in place of a 5% monoglyceride.

EXAMPLE 21

The procedure of Example 1 is followed except that heparin is added in a quantity that will yield 1000 units/ml per unit dose in the finished product in place of erythromycin.

EXAMPLE 22

The procedure of Example 1 is followed except that regular insulin is added in a quantity that will yield a finished product containing 40 units of insulin/cc per unit dose is used in place of erythromycin.

EXAMPLE 23

The procedure of Example 1 is used except that regular insulin is added in a quantity that will yield a finished product containing 100 units/cc of regular insulin per unit dose in place of erythromycin.

EXAMPLE 24

The procedure of Example 1 is followed except that protaglandin E is added in a quantity that will yield 20 mg/ml per unit dose in the finished product in place of erythromycin.

EXAMPLE 25

The procedure of Example 5 is followed except that heparin is added in a quantity that will yield a finished product containing 1000/ml per unit dose is used in place of erythromycin.

EXAMPLE 26

The procedure of Example 5 is followed except that regular insulin is added in a quantity that will yield a finished product containing 40 units of insulin per unit dose in place of erythromycin.

EXAMPLE 27

The procedure of Example 6 is followed except that heparin is added in a quantity that will yield 1000 units/ml per unit dose in the finished product is used in place of erythromycin and the preparation is heated to 36° C. for 15 seconds.

EXAMPLE 28

The procedure of Example 6 is followed except that regular insulin is added in a quantity that will yield 40 units of insulin/cc per unit dose in the finished product; said product is heated at 36° C. for 15 seconds.

EXAMPLE 29

The procedure of Example 14 is followed except that heparin is added in a quantity that will yield a finished product containing 1000 units/ml per unit dose in place of erythromycin.

EXAMPLE 30

The procedure of Example 14 is followed except that insulin is added in a quantity that will yield a finished product containing 40 units/cc per unit dose in place of erythromycin.

EXAMPLE 31

The procedure of Example 15 is followed except that a quantity of heparin that will yield the equivalent of 1000 units/ml per unit dose in the finished product is added in place of erythromycin and the composition is heated at 35°–36° C. for 15 seconds.

EXAMPLE 32

The procedure of Example 15 is used except that a quantity of regular insulin is added that will yield the equivalent of 40 units/cc in a unit dose of the finished product in place of erythromycin. The composition is then heated at 36° C. for 10 seconds.

EXAMPLE 33

The procedure of Example 5 is followed except that a quantity of prostaglandin is added that will yield a finished product containing 20 mg per unit dose in place of erythromycin.

EXAMPLE 34

The procedure of Example 14 is followed except that a quantity of gentamicin sulfate is added that will yield a finished product containing 3.0 mg per unit dose in place of erythromycin.

EXAMPLE 35

The procedure of Example 15 is used except that gentamicin is added in a quantity that will yield a finished product containing 3.0 mg per unit dose in place of erythromycin.

EXAMPLE 36

The procedure of Example 20 is followed except that a quantity of gentamicin is added that will yield a finished product containing 3.0 mg per unit dose in place of erythromycin.

EXAMPLE 37

The procedure of Example 20 is followed except that the colloid rich phase and the colloid poor phase are derived from a coacervate system based upon a preparation comprised of 3% w/v albumin and 3% w/v lecithin and a solution comprised of 3% monoglyceride, 4% diglyceride and 3% triglyceride is used in place of the monoglyceride solution.

EXAMPLE 38

The procedure of Example 27 is used except that regular insulin in an amount that will result in a finished product containing 40 units/cc per unit dose is used in place of erythromycin.

EXAMPLE 39

The procedure of Example 1 is followed except that 1 mg of Atrial Peptide 3 in 5 mls of the colloid rich phase is substituted for the erythromycin component. Atrial Peptide 3 is a biological which comprises a group of very similar proteins produced in the heart and which is, when incorporated in the present invention, useful in the treatment of cardiovascular disease.

EXAMPLE 40

The procedure of Example 3 is followed except that 1 mg of Atrial Peptide 3 in 5 mls of the colloid rich phase is substituted for the erythromycin component.

EXAMPLE 41

The procedure of Example 5 is followed except that 1 mg of Atrial Peptide 3 in 5 mls of the colloid rich phase is substituted for the erythromycin component.

EXAMPLE 42

The procedure of Example 14 is followed except that 1 mg of Atrial Peptide 3 in 5 mls of the colloid rich phase is mixed into the colloid rich phase as a substitute for the erythromycin component.

EXAMPLE 43

The procedure of Example 20 is followed except that a composition comprised of 1 mg of Atrial Peptide 3 in 5 mls of the colloid rich phase is substituted for the erythromycin component.

EXAMPLE 44

The procedure of Example 37 is used except that a composition comprised of 1 mg of Atrial Peptide 3 in 5 mls of the colloid rich phase is substituted for the erythromycin component.

EXAMPLE 45

The procedure of Example 37 is followed except that regular insulin in an amount that will yield 40 cc per unit dose in the finished product is used in place of erthromycin.

I claim:

1. A method of preparing a composition for oral delivery of a pharmaceutical component; said method based upon a non-toxic liquid aqueous two phase coacervate system;
   (a) one of said phases being an aqueous colloid rich phase, semi-polar to non-polar in character;
   (b) the other of said phases being an aqueous colloid poor phase, semi-polar to polar in character;
   (c) said colloid rich phase being insoluble and in equilibrium with said colloid poor phase;
   (d) said two phase system prepared from water and one or more surfactants selected from the group consisting of anionic, cationic, amphoteric, and non-ionic surfactants, polysaccharides, synthetic polymers, polysorbates and their derivatives and mixtures thereof;
   (e) said two phase system further prepared to contain a pharmaceutical component in the colloid poor phase of the coacervate system.

2. The composition according to claim 1, wherein the pharmaceutical component is selected from drugs, their salts and derivatives thereof; biologicals, enzymes and any other pharmacologically active compositions and their derivatives, and mixtures thereof.

3. The composition according to claim 1 or 2, wherein the colloid rich phase comprises from 0.5% to 99.5% by volume, and the colloid poor phase comprises from 99.5% to 0.5% by volume of the two phase liquid aqueous system.

4. The composition according to claim 1, wherein the surfactant comprises a mixture of a polysaccharide and a synthetic polymer.

5. The composition according to claim 4, wherein the polysaccharide is dextran and the synthetic polymer is polyethylene glycol.

6. The composition according to any of claims 1, wherein the colloid rich phase is separated from the colloid poor phase and the pharmaceutical component is added to said colloid rich phase.

7. The composition according to claim 6, wherein the pharmaceutical component contains a glyceride selected from a monoglyceride, diglyceride, triglyceride and mixtures thereof.

8. The composition according to claim 7, wherein the two phases are recombined and emulsified to yield a drug delivery system in the form of an emulsion.

9. The composition according to claims 6 or 7, wherein lecithin is dispersed into the colloid rich phase; and the two phases are recombined and microemulsified to yield a drug delivery system in the form of a microemulsion.

10. The composition according to claims 6 or 7, wherein lecithin, albumin and the colloid poor phase are combined with the colloid rich phase and microemulsified; said microemulsion being further subjected to a heating or chemical step to yield a sustained release drug delivery system.

11. A composition as defined according to claims 6 to 8, wherein the final product is in any appropriate dosage form including liquid, granule, tablet and suspension.

12. A method of preparing a composition useful as an oral delivery system; said method based upon a non-toxic liquid aqueous two phase coacervate system;
   (a) one of said phases being an aqueous colloid rich phase, semi-polar to non-polar in character;
   (b) the other of said phases being an aqueous colloid poor phase, semi-polar to polar in character;
   (c) said colloid rich phase being insoluble and in equilibrium with said colloid poor phase;
   (d) said two phase system prepared from water and one or more surfactants selected from the group comprising anionic, cationic, amphoteric, and non-ionic surfactants, polysaccharides, synthetic polymers, and polysorbates and their derivatives;
   (e) said two phase system further prepared to contain a pharmaceutical component in the colloid poor phase of the coacervate system.

13. The method according to claim 12, wherein the pharmaceutical component is selected from drugs, their salts and derivatives thereof; biologicals, enzymes and any other pharmacologically active compositions and their derivatives, and mixtures thereof.

14. The method according to claim 12, wherein the surfactant is a mixture of a polysaccharide and a polysorbate.

15. The method according to claim 14, wherein the polysaccharide is dextran and the polysorbate is polyethylene glycol.

16. The method according to claim 15, including the steps of:
   (a) mixing a solution of dextran into a solution of polyethylene glycol;
   (b) storing the mixture undisturbed and at room temperature or under conventional refrigeration for from 6 to 24 hours until the composition of step (a) separates into two layers, one above the other, the lower phase being the colloid rich phase, the upper phase being the colloid poor phase; separating the two phases; and mixing a desired quantity of the pharmaceutical component into the colloid poor phase.

17. The method according to claim 16, further including the step of adding a solution of NaCl to the mixture dropwise to aid in separating the two phases.

18. A method of preparing a composition for oral delivery of a pharmaceutical component; said method based upon a non-toxic liquid aqueous two phase coacervate system;
   (a) one of said phases being an aqueous colloid rich phase, semi-polar to non-polar in character;
   (b) the other of said phases being an aqueous colloid poor phase, semi-polar to polar in character;
   (c) said colloid rich phase being insoluble and in equilibrium with said colloid poor phase;
   (d) said two phase system prepared from water and one or more surfactants selected from the group consisting of anionic, cationic, amphoteric, and non-ionic surfactants, polysaccharides, synthetic polymers, polysorbates and their derivatives and mixtures thereof;
   (e) said two phase system further prepared to contain a pharmaceutical component in the colloid rich phase of the coacervate system.

19. The method according to claim 18, further including the additional steps of:
   recombining the colloid poor phase with the colloid rich phase, and
   emulsifying the combined colloid poor and colloid rich phases to produce an oral delivery composition in emulsion form.

20. The method according to claim 18, further including adding a solubilizing agent to the colloid rich phase; mixing the colloid poor phase with the colloid rich phase and emulsifying the product to produce an oral delivery composition in microemulsion form.

21. The method according to claim 20, wherein the solubilizing agent is a phospholipid.

22. The method according to claim 18, further including the steps of adding a phospholipid and a protein to the colloid rich phase; mixing the colloid poor phase with the colloid rich phase; emulsifying the composition to produce a microemulsion of the colloid rich phase in particles containing the pharmaceutical component; and encapsulating the particles using a chemical crosslinking agent or heat, to produce an oral drug delivery system in the form of encapsulated microparticles.

23. The method according to claim 21, wherein the protein is albumin.

24. The method according to claim 21, wherein the cross-linking agent is a non-toxic aldehyde.

25. The method of claim 21, which yields sustained release particles containing the pharmaceutical component.

26. The method according to claim 22, wherein the pharmaceutical component is dissolved in a monoglyceride, diglyceride or triglyceride solution or a mixture thereof prior to addition to the colloid rich phase to provide time release particles containing the pharmaceutical component; ranging from prompt release to sustained release particles.

27. The method according to claim 12, wherein the pharmaceutical component is selected from drugs, their salts and derivatives thereof; biologicals, enzymes and any other pharmacologically active compositions and their derivatives, and mixtures thereof.

28. The method of claim 21 wherein the phospholipid is lecithen.

29. A method of introducing a pharmaceutical component into a circulatory system comprising orally ingesting a composition comprising an aqueous coacervate system including water, a surface active agent and an effective amount of the pharmaceutical component, said coacervate system including an aqueous coacervate-based film encapsulating the pharmaceutical compound; said aqueous coacervate-based film comprising an aqueous colloid-rich phase, or an aqueous colloid poor phase, or a combination thereof.

* * * * *

UNITED STATES PATENT AND TRADEMARK OFFICE
CERTIFICATE OF CORRECTION

PATENT NO. : 4,794,000

DATED : December 27, 1988

INVENTOR(S) : Bernard Ecanow

It is certified that error appears in the above-identified patent and that said Letters Patent is hereby corrected as shown below:

Col. 15, line 14; "21" should read --22--;

Col. 15, line 16; "21" should read --22--;

Col. 15, line 18, "21" should read --22--;

Col. 16, line 18; "compound" should read --component--.

Signed and Sealed this

Fifteenth Day of August, 1989

*Attest:*

DONALD J. QUIGG

*Attesting Officer*   *Commissioner of Patents and Trademarks*